United States Patent [19]

Teller et al.

[11] 4,038,029

[45] July 26, 1977

[54] LIMULUS LYSATE TURBIDITY TEST FOR PYROGENS

[75] Inventors: Joseph D. Teller, Freehold; Kristine M. Kelly, Manasquan, both of N.J.

[73] Assignee: Worthington Biochemical Corporation, Freehold, N.J.

[21] Appl. No.: 650,607

[22] Filed: Jan. 20, 1976

[51] Int. Cl.$^2$ .................. G01N 21/00; G01N 33/16; C12K 1/00

[52] U.S. Cl. .................. 23/230 B; 195/103.5 R; 252/408; 424/12; 424/95

[58] Field of Search .............. 23/230 B; 195/103.5 R; 252/408; 424/12

[56] References Cited

U.S. PATENT DOCUMENTS

| | | | |
|---|---|---|---|
| 3,915,805 | 10/1975 | Levin | 23/230 B |
| 3,944,391 | 3/1976 | Harris | 23/230 B |
| 3,954,663 | 5/1976 | Yamamoto | 424/12 X |

*Primary Examiner*—Sidney Marantz
*Attorney, Agent, or Firm*—Kenyon & Kenyon, Reilly, Carr & Chapin

[57] ABSTRACT

A sample of an aqueous liquid, e.g. an aqueous parenterally-administered drug, is tested for determining the amount of any endotoxin contained therein by admixing a sample of the liquid with lysate obtained by water lysing washed amebocyte cells from the blood of the horseshoe crab (Limulus polyphemus), said lysate being buffered at a pH between about 6.5 and about 6.8 and being at a concentration such that 1 ml thereof is reactive with 0.1 ml of an endotoxin solution containing 1 ng per ml of endotoxin to develop upon incubation for 60 minutes at 37° C turbidity exhibiting absorbancy between about 0.07 and about 0.2 at 360 nm, incubating the resulting admixture under temperature and time conditions conducive to increase in absorbancy resulting from reaction between said lysate and any endotoxin contained in the sample and determining the absorbancy of the resulting admixture ordinarily in relation to the absorbancy similarly obtained by reaction of the same lysate with one or more solutions of known endotoxin content, whereby the endotoxin content of the sample may be determined not only qualitatively but also quantitatively.

19 Claims, No Drawings

LIMULUS LYSATE TURBIDITY TEST FOR PYROGENS

FIELD OF THE INVENTION

This invention relates to the testing of aqueous liquids for the presence therein of a pyrogen, namely, a substance which when present in the blood of a mammal induces fever. The most extensive application of this invention is in connection with the testing of parenterally-administered aqueous liquids, although it has other applications.

BACKGROUND OF THE INVENTION

All parenteral drugs are potentially hazardous in that during any stage in their production they can become contaminated. Rigid control by final testing for the presence of bacteria has been in practice for many years and standardized sterility tests such as those described in the U.S. Pharmacopoeia have proven to be adequate and effective safeguards. The problem of pyrogens, however, while controllable, is much more difficult and testing procedures are tedious, expensive and not always reproducible. As aforesaid, pyrogens are fever-causing substances, generally lipopolysaccharides which are liberated as endotoxins by gram-negative bacteria. During the processing of a drug all bacterial cells may be removed and the drug may test "sterile", yet pyrogens may still be present which could cause serious reactions when injected. For this reason all parenteral drugs must be tested for pyrogens by a procedure similar to that described in the U.S. Pharmacopoeia wherein a group of rabbits is injected intravenously with a specified amount of the drug and the resultant average temperature rise, if any, over a period of three hours is observed. Because of the obvious variation encountered in a biological test such as this, steps must be taken all along the testing procedure to ensure that conditions are as uniform and standardized as is possible. This demands a special laboratory where animals can be maintained in a basal state and an adequate supply of animals such that there is an ample recovery period between tests.

Despite the difficulties in maintaining uniform conditions, the test has proven extremely useful and is relied upon on a worldwide basis to keep pyrogenic drug reactions to a minimum. Yet a simplified, in vitro type of procedure could reduce enormously the costs of time and materials for conducting this important test. Furthermore, there are certain types of drugs, e.g. short lived radio-labeled diagnostics, cisternographic agents and certain classes of hypnotics that by their nature are precluded from the rabbit fever pyrogen test. These materials must now be used at the risk of not being pyrogen-free.

The necessity for testing an aqueous liquid containing dissolved or dispersed therein a drug such as codeine or an antibiotic, or other substance which has a medicinal function also extends to solutions or dispersions of other substances which are parenterally-administered and which are to be regarded herein and in the claims as drugs in a broad sense such as solutions of sodium chloride or of glucose that are intravenously administered or a solution or dispersion of any of various nutrients used in intravenous feeding. The necessity of testing for the possible presence of pyrogens also extends to bottles and other containers for parenterally-administered liquids and likewise to tubing, injection needles and other instrumentalities used in the parenteral administration of drugs or used in connection with transfusions or infusions. Testing for contamination by pyrogens also has application to water and saline solutions intended for use in parenterally-administered solutions as well as for other purposes. For example, the presence of pyrogen in potable water has been shown to have a definite relationship to bacteria population. Testing for the presence of pyrogens also has other applications such as the determination of their possible presence in certain of the body fluids of mammals.

An indication that an in vitro test might be available appeared several years ago when it was discovered that the circulating cell, the amebocyte, in the blood of the horseshoe crab (Limulus polyphemus) contains a group of proteins that react with low levels of endotoxins. Evidence was obtained to show that one of three proteins, probably a proteolytic enzyme, is activated in some as yet unknown manner by endotoxin after which it causes another protein to coagulate or gel. The protein mixture (lysate) may be isolated from the amebocytes and used as a reagent to detect the presence of endotoxin by noting the formation of a gel after incubating lysate and endotoxin for an hour or more.

In the test procedure most generally employed heretofore the lysate is prepared by washing the amebocyte cells contained in the blood of the horseshoe crab so as to remove the components of the blood other than the amebocyte cells. This usually is accomplished using water containing sodium chloride in order to minimize premature deterioration of the walls of the cells. Preferably, the washing solution also contains calcium chloride. The washing also is accomplished in the presence of N-ethylmaleimide which has been found to be effective in preventing the aggregation of amebocyte cells so that they may be separated more readily from the aqueous wash water by centrifugation. Two such washings followed by centrifugation are normally sufficient. The washed cells thereafter are lysed using 2 volumes of water for each volume of the washed cells. After the lysing has been completed, as by agitating the suspended cells, the protein content of the cells becomes dispersed in the water, which becomes the "lysate" after the separation of the cell debris by centrifugation. Other lysing techniques also are known.

In carrying out the gel test hereinabove mentioned, it has been the usual practice heretofore to add 0.1 ml of the aqueous solution as prepared for parenteral administration to 0.1 ml of the lysate such as that produced as previously described. After incubation of the mixture at 37° C for 1 hour the mixture is examined for gel formation. If gel is formed, this is an indication of the presence of an endotoxin due to coagulation of the protein content in the lysate. The usual manner of evaluation as to whether or not a gel has formed is by the ability of the mixture to remain in the tube in which the test is carried out when the tube is inverted. Usually the test also is run with a known level of endotoxin as a comparative standard. However, because of variation from lot to lot of lysate and variation in the nature of different endotoxins, gel formation is not always uniform and evaluation often becomes a subjective determination. Further, for very low levels of endotoxin, the incubation period is prolonged and occasionally a thickening of the mixture is observed or a formation of granules without the formation of a solid clot thereby rendering the test even more difficult to evaluate.

GENERAL STATEMENT OF THE INVENTION

It is an object of this invention to provide an in vitro test for not only the qualitative but also the quantitative determination of the endotoxin content in an aqueous liquid which, except for the presence therein of endotoxin, is physiologically compatible with humans and other mammals and which when administered to or otherwise is present in a human or other mammal is such as to serve as a vehicle for endotoxins, if present, that induce fever. For purposes of brevity, any such liquid to be tested for the possible presence therein of endotoxin is referred to herein and in the claims as the "aqueous liquid" used in the test procedure.

It is a further object of this invention to provide a test procedure such that quantitative response to the presence of an endotoxin may be manifested in such a way that a concrete reading may be had which reflects the amount of endotoxin in the sample of aqueous liquid being tested.

More particularly, it is an object of this invention to provide a test procedure such that the response to endotoxin content in a sample of the aqueous liquid may be measured in terms of variation in absorbancy that is quantitatively proportional to the endotoxin concentration in the sample using conventional optical instrumentation such as a spectrophotometer.

According to this invention, a sample of the aqueous liquid to be tested is admixed with a lysate which is the product of water lysing washed amebocyte cells, said lysate being buffered at a pH between about 6.5 and about 6.8 and diluted so as to be at a concentration such that 1 ml thereof is reactive with 0.1 ml of an endotoxin solution containing 1 ng per ml of endotoxin to develop upon incubation for 60 minutes at 37° C turbidity that imparts an absorbancy between about 0.07 and about 0.2 using 360 nm light. As more explicitly disclosed hereinbelow, said concentration is much more dilute than the lysate as conventionally produced and used in the above-mentioned gel test. When diluted so as to occur within the aforesaid concentration range limits we have found that the turbidity induced by the presence of an endotoxin is such that response to the endotoxin may be optically determined in a sensitive and accurately reproducible manner by measuring the absorbancy of light of a given wavelength, e.g, 360 nm. In this manner the presence of endotoxin can be readily determined in vitro utilizing the convenience and accuracy incident to the use of a spectrophotometer or other equivalent instrument.

In practicing this invention the admixture of the aqueous liquid sample and said lysate is incubated under temperature and time conditions conducive to increase in absorbancy by reason of turbidity induced responsive to reaction between the lysate and the endotoxin content of the sample and the absorbancy of the incubated admixture is determined. In the ordinary case the sample of the aqueous liquid is a sample of aqueous liquid which has been prepared for parenteral administration and, in such case, in making the test 0.1 ml of the liquid as so prepared is admixed with 1 ml of lysate prepared so as to be within the aforesaid critical dilution range. In preferred practice, the determination thus obtained is compared with the determination obtained in the same way in the case of a similarly prepared admixture with the same lysate but using an endotoxin solution of known concentration. For purposes of comparison using the same lysate, additional measurements are made using endotoxin solutions of different known concentrations so that a curve may be prepared against which the measurement ascertained in the case of a sample of an unknown may be read.

We have found that when the lysate is buffered within the aforesaid range and is diluted so as to be at a concentration meeting the aforesaid requirements the response to endotoxin content under the conditions aforesaid is such that the absorbancy reading is in direct relation to said endotoxin content. We also have found that under these conditions the responsiveness to endotoxin is extremely sensitive so that endotoxin contents may be detected which are not ascertainable in the case of the rabbit fever testing that currently is widely resorted to. Detection of as little as $10^{-12}$ gms of actual amount of endotoxin has been detected using the method of this invention. It also is the case that the endotoxin content may be measured much more accurately than is possible when employing the gel test as heretofore suggested. Moreover, we have found that in certain instances it has been possible in the practice of this invention to detect the presence of endotoxin which is not revealed when using the gel test.

When practicing this invention it has been found to be convenient to follow the previous practices that have heretofore been used in the preparation of the lysate as described hereinabove. The protein content of the lysate thus produced is such that extensive dilution is required in order to comply with the concentration requirement hereinabove mentioned as essential for use in the practice of this invention. In the case of a lysate prepared as above-described, this involves a 20 to 22-fold dilution of the lysate with a buffer at a pH from about 6.5 to about 6.8. The buffered diluted lysate then is tested in the manner hereinabove described to determine whether the absorbancy is within the range from about 0.07 to about 0.2. If the absorbancy is not within this range, then the dilution of the lysate is adjusted so that the concentration requirement may be satisfied. While it is usually convenient to initially obtain a lysate using 2 volumes of water for each volume of washed cells, this is not essential since it is the diluted concentration of the lysate used when performing the absorbancy determination that is critical regardless of the concentration of the lysate as initially produced. The buffered lysate solution may be used immediately for producing a curve based on known endotoxin solutions of different concentrations followed by such additional measurements as may be desired for measuring the endotoxin content of different samples of aqueous liquids to be tested. Such testing necessarily has to be accomplished promptly since the buffered solution remains stable for only about 2 hours.

In order to prepare a reagent suitable for storage and subsequent use by a laboratory, as is the usual case in connection with the practice of this invention, a quantity of a lysate prepared as above described and prior to dilution is admixed with a buffer in sufficient quantity to provide a pH within the range from about 6.5 to about 6.8 when said undiluted quantity has been diluted to the concentration which is required for meeting the absorbancy test hereinabove referred to and which has been ascertained by directly adjusting the concentration of the lysate. Thereupon the admixture of said quantity of lysate and buffer is reduced to dryness by lyophilization. In the lyophilized state the lysate may be stored at a temperature of about 2° to 6° C for a substantial period of time that enables the prepared material to be distributed for later laboratory test purposes. We have found that in the practice of this invention "pipes" buffer, namely 1,4 piperazine bis-(ethane sulfuric acid), has the specific property, as compared with other buffers such as a phosphate buffer, of imparting, as regards the reactivity of the lysate with endotoxin, improved stability against deterioration in the unrefrigerated state. Saline or phosphate buffers or water per se exhibit some absorbancy which preferably should be low in order to afford optimum optical properties when performing the absorbancy test. Phosphate buffer such as $Na_2HPO_4$—$KH_2PO_4$ was found to exhibit optimum properties of low initial absorbancy and responsive reactivity to endotoxin when used so as to occur in the testing solution as made up for carrying out the test at a concentration of about 0.025M. However, while stability and reactivity with endotoxin of the order aforesaid may be had using phosphate buffer, for survival under shipping and storage conditions often encountered, a higher order of stability is desirable and can be had by the inclusion in the buffer of pipes buffer in effective amount so as to substantially improve stability as compared with phosphate buffer of like molarity. Optimum combined properties of low initial absorbance and high stability have been found to occur when the final test solution contains about 0.0125M of phosphate buffer and about 0.0125M of pipes buffer. However, pipes buffer by itself while affording high stability, also exhibits initial absorbancy that is only slightly greater than that exhibited by phosphate buffer and may be used as the sole buffer. A common heat stress test that is resorted to in order to provide assurance against excessive instability in shipment and storage is that of storage at 40° C for three days. The increased stability which results from the presence of pipes buffer is evidenced by the following data showing absorbancy induced initially and at increasing endotoxin levels of 0.025M phosphate buffer, 0.0125M pipes buffer and a mixture of 0.0125M phosphate buffer, 0.0125M pipes buffer and a mixture of 0.0125M phosphate buffer with 0.0125M pipes buffer, the concentration being that occurring in the final test solution. Lysate in an amount which affords an absorbancy of about 0.1 under the aforesaid conditions of test was lyophilized with the above-mentioned buffers, and the absorbancy obtained after three days' refrigeration at 5° C were compared with the absorbancy obtained after storing for 3 days at 40° C and the following data were obtained:

| Endo-toxin ng/ml | 0.025M Phosphate Absorbance | | 0.025M Pipes Absorbance | | 0.0125M Phosphate 0.0125M Pipes Absorbance | |
|---|---|---|---|---|---|---|
| | 5° C | 40° C | 5° C | 40° C | 5° C | 40° C |
| 0.0000 | .055 | .147 | .158 | .167 | 0.123 | .114 |
| 0.0625 | .131 | .146 | .184 | .182 | 0.167 | .150 |
| 0.125 | .190 | .141 | .212 | .210 | 0.245 | .202 |
| 0.25 | .309 | .145 | .267 | .300 | 0.406 | .433 |
| 0.50 | .431 | .145 | .498 | .441 | 0.506 | .499 |

As appears from the foregoing data, the phosphate buffer was not stable when subjected to 40° C for 3 days while the buffered lysate retained its activity essentially unimpaired in the case of pipes. It also is indicated that optimum combined properties of low initial absorbancy and retained high absorbancy after three days at 40° C were afforded using the blend of phosphate and pipes buffers.

At the time of use the lyophilized undiluted lysate admixed with the buffer is reconstituted with an amount of water which provides the required lysate concentration which has been described hereinabove and which is essential in the practice of this invention. The preliminary evaluation of a particular lysate in relation to solutions of known endotoxin content is required due to the fact that the protein content of the amebocyte cells exhibits a certain amount of variation. More importantly, the reactivity of endotoxin with the protein content of the amebocyte cells varies quite substantially depending on such factors as geographical location of the horseshoe crabs that are used and the season of the year. Consequently it is necessary in the case of any given lysate to make the proper adjustment in concentration by dilution on a largely empirical basis based on prior experience so as to exhibit the necessary absorbancy response under the conditions hereinabove mentioned. If the desired concentration is not initially achieved, the concentration may be adjusted and the known manner of adjustment may be be availed of utilizing a portion of the originally obtained lysate that is reduced to dryness by lyophilization in the presence of a required amount of buffer and that at the time of use may be reconstituted to the required lysate concentration by the addition of a stated amount of water.

In the case of a lysate prepared by lysing washed amebocyte cells using 2 volumes of pure water for each volume of washed cells, it is usually convenient to employ 0.5 ml of the lysate and adjust the concentration so that the 1 ml of the diluted lysate when buffered at a pH of between 6.5 and 6.8 is reactive with 0.1 ml of an endotoxin solution known to contain 1 ng per ml of endotoxin to provide an absorbancy within the required range. Having made this determination, then a basis is provided such that 0.5 ml of the same lysate may be admixed with a corresponding amount of buffer and reduced to dryness by lyophilization and such that at the time of use the lyophilized lysate may be reconstituted using an amount of water appropriate for accomplishing the concentration required for testing. When, for example, 0.5 ml of the lysate is lyophilized, 11 ml of pure water may be used to reconstitute the buffered lysate so as to provide the required concentration. This is a convenient practice since sufficient solution may be provided for making ten test measurements, some in relation to endotoxin solutions of known concentration for providing a standard curve, the additional solution being available for making test determinations in connection with samples of drugs on other aqueous liquids of unknown endotoxin content. In this manner a method of testing is provided such that notwithstanding variations in the reactivity of the protein as between different horseshoe crab sources, the endotoxin content of an aqueous liquid may be measured with a high degree of accuracy and with an extraordinarily high degree of sensitivity in ascertaining the presence of extremely small quantities of endotoxin.

The term "absorbancy" is employed herein in the conventional meaning as being the negative logarithm of transmittancy and when $T_s$ designates the transmittance of a given solution the absorbancy ($A_s$) may be represented as follows:

$$A_s = \log 1/T_s$$

the transmittancy $T_s$ being the ratio of transmittance of the solution to that of the solvent absent the solute as represented by the expression:

$$T_s = \frac{\text{Transmittance of solution}}{\text{Transmittance of solvent}}$$

the transmittance of the solution and the transmittance of the solvent being measured under like conditions of wavelength (here 360 nm), incident light intensity and length of travel through the solution, normally 1 cm. Absorbancy as measured above also is referred to as optical density, the values being the same.

This invention has wide application in the testing of an aqueous liquid as it exists in some suitable container in condition for use without change for parenteral injection. In the case of drugs or other substances which are initially produced at some other concentration or in the dry state, the test of this invention may be carried out by adjusting the concentration of the drug or other substance as by the addition of water or saline solution so that the resulting aqueous solution occurs in the condition including concentration as adapted for use for parenteral injection. In such case the water or saline per se that is used to bring the solution to proper concentration should be tested for the presence of endotoxin in the manner hereinabove described, namely, by the addition of 0.1 ml thereof to 1 ml of lysate that is within the critical dilution range hereinabove described. It also is the case that, if desired, a solution of a drug or other substance that is at some other concentration than that suitable for parenteral injection may be employed in the test procedure if the turbidity response is favorable for measuring absorbancy induced by the presence of endotoxin. Occasionally it is desirable to test for the possible presence of endotoxin in a drug that is applied topically and that when so applied becomes absorbed sufficiently to enter the blood stream. In such case, when the composition of the drug permits, the drug is brought into the form of an aqueous liquid by the addition of water or saline as above described to provide a concentration that is suitable for testing when adding 0.1 ml to 1 ml of the diluted lysate. If necessary, the tests of the character aforesaid may be repeated at different solution concentrations for attaining the turbidity that is the most favorable for measuring absorbancy.

Contamination of containers, tubing, injection needles, etc. due to endotoxins may be determined in the practice of this invention by rinsing the instrumentalities or other equipment with a small amount, e.g. about 40 ml, of water or a physiological saline such as 0.85% sodium chloride at a slow rate such as 10 ml per minute. The aqueous rinsing liquid may then be tested for the presence of endotoxin as hereinabove described, namely, by the addition of 0.1 ml thereof to 1 ml of the lysate that is within the above-defined critical dilution range.

When testing water such as that supplied by a municipality for the purpose of revealing bacterial contamination evidenced by the presence of endotoxin, the endotoxin content may be so great that when 0.1 ml thereof is mixed with 1 ml of the lysate at the critical dilution aforesaid, the resulting turbidity results in absorbancy in excess of the range from about 0.07 to about 0.2. In such case the water to be tested is diluted with known amounts of water known to be essentially pyrogen-free until, when tested, the absorbancy is within this range. It follows that the pyrogen content of the undiluted water will be a function of the pyrogen content of the diluted water depending on the known extent of the dilution. The procedure also has application to aqueous liquids other than water.

More generally, the test procedure and composition herein described is applicable whenever it is desired to test for the possible presence of endotoxins in an aqueous liquid. For example, the presence of endotoxin in urine may be determined by admixing 0.1 ml of urine with 1 ml of the lysate within the aforesaid critical dilution range. The presence of endotoxin in spinal fluid may be similarly determined.

In the event that the liquid sample to be tested may per se exhibit some turbidity which contributes to the total absorbancy exhibited when the sample is tested as herein described, it normally is desirable to determine the absorbancy attributable to the sample per se by mixing 0.1 ml of the sample with 1 ml of the same buffer solution that is employed in the diluted lysate used for determining total absorbancy and subtract the absorbancy due to the turbidity of the sample from the total absorbancy obtained when 0.1 ml of the sample is incubated with the 1 ml of the diluted lysate. The difference provides the absorbancy due to the antigen content of the sample. The determination of absorbancy of the sample per se also normally is determined in like manner when the sample is a colored liquid such as urine, i.e., absorbancy is measured when 0.1 ml of the colored liquid is mixed with 1 ml of buffer solution in the absence of the lysate and the absorbancy so measured is subtracted from the absorbancy of the sample when mixed in like amount with a like amount of the diluted lysate.

When utilizing lysate that has been diluted so as to provide the above-stated absorbancy under the test conditions hereinabove described, namely, such that 1 ml is reactive with 0.1 ml of an endotoxin solution containing 1 mg per ml of endotoxin to develop upon incubation for 60 minutes at 37° C turbidity that imparts an absorbancy between about 0.07 and about 0.2 at 360 nm, it ordinarily is preferable when measuring the endotoxin content of a liquid of unknown endotoxin content to measure absorbancy at 360 nm. However, provided the diluted lysate meets the aforesaid requirements, the endotoxin content of an unknown may be determined whether the absorbancy is measured at the same or at some wavelength other than 360 nm such as 340 nm provided the absorbancy of the unknown is measured at the same wavelength as that used in the preparation of the standard curve with which it is compared. Analogously, and subject to the aforesaid proviso, the time and temperature employed in incubation may be varied as by employing a somewhat longer incubation period at somewhat lower temperature so long as the turbidity response is sufficient in order to detect endotoxin content with desired sensitivity. However, incubation for 60 minutes at 37° C and determination of absorbancy at 360 nm provide the optimum conditions that ordinarily are employed in the practice of this invention.

The test procedure of this invention has general applicability except in rare instances when the liquid to be tested contains a substance such as an inhibitor which inhibits the development of turbidity to such extent that the test does not accurately reflect the actual amount of any endotoxin that may be present. Carbenacillin is an example of a substance which when in solution suitable for parenteral injection contains something that interferes with the turbidity response. In the vast majority of applications of the test procedure of this invention there is no necessity for checking for the possible presence of an inhibitor especially after experience has demonstrated that the respective parenterally administered drugs or other aqueous liquids under consideration for the test as conventionally supplied present no problem as regards the possible presence of an inhibitor or some other substance that interferes with the turbidity response. However, in applying the test procedure to a type of material which has not previously been subjected to the test procedure, the precaution advisedly should be taken of checking for the possible presence of an interfering substance. In the first instance, such checking may be accomplished by adding aqueous liquid to be tested, e.g. 0.1 ml to a mixture of 1 ml of lysate within the critical dilution range aforesaid and a known quantity of endotoxin such as 0.1 ml of an endotoxin solution containing 1 ng per ml of endotoxin. If the turbidity is less than that developed by the endotoxin in the absence of the additional substance under consideration for testing, the presence of an inhibitor is indicated. If, on the other hand, there is no decrease in turbidity, the additional precaution may be taken of checking by the rabbit inoculation procedure whether or not the material in question is free of endotoxin. Once this precaution has been taken and it has been established that the material in question as conventionally furnished is free of any inhibitor the test procedure may be repeated again and again without checking for the possible presence of an inhibitor. In the event that an inhibitor is found to be present, the test procedure of this invention will not be applicable in the absence of providing some expedient for counteracting the inhibitor.

DESCRIPTION OF SPECIFIC EXAMPLE

Several live horseshoe crabs are obtained and bled by inserting a large bore hypodermic needle into the joint of the thoracic and abdominal segments and the blood is collected in 250 ml cups containing 50 ml of a mixture of 0.125% N-ethyl-maleimide, 3% NaCl and 0.02M $CaCl_2$. The blood is then centrifuged at 750 G force for 10 minutes. The precipitate of sedimented amebocytes is retained and resuspended in one-half the original volume of the above mixture. The cells are centrifuged again, the supernatant is poured off and water equal to approximately twice the volume of the cells is added. The cell suspension is then placed in a shaker in a cold room and lysed for two days at 5° C. The suspension is centrifuged at 26,000 G, the supernatant is retained and the cell debris is discarded. The supernatant is the lysate containing the proteins derived from the washed amebocyte cells.

0.5 ml of the lysate is diluted with 11 ml of water containing sufficient phosphate-pipes buffer to provide a pH of about 6.8. 1 ml of the diluted lysate is mixed with 0.1 ml of a solution containing 1 ng per ml of endotoxin. For purposes of uniformity of endotoxin, the solution desirably is that which is standardized by the FDA under the designation "Klebsiella". The resulting admixture is incubated for 60 minutes at 37° C, whereupon it is transferred to a microcuvette in which the absorbancy at 360 nm is measured utilizing the well-known standard procedures for measuring values of absorbancy. Under these testing conditions optimum concentration of the lysate is indicated if the absorbancy is substantially 0.15, although, as aforesaid, the tolerance may vary between about 0.07 and about 0.02. If the optical density is not within this range, then the concentration is adjusted until the requirements for optical density are met. Such adjustment results in a variation in the quantity of lysate which, when diluted with 11 parts of water, will provide a concentration meeting the requirements for providing the proper absorbancy. In other words, the adjusted amount of lysate may be slighty more or slightly less than 0.5 ml.

If it is the case that 0.5 ml meets the requirements for providing the required absorbancy, the lysate may be provided in lyophilized form by adding to 0.5 ml of the lysate buffer pH 6.8, provided by 0.05M of pipes buffer and 0.05M phosphate buffer, and water such that the final volume is 2.5 ml. The vial containing this reagent mixture is then subjected to lyophilization to reduce the contents to dryness. If a quantity somewhat greater or less than 0.5 ml provides the proper absorbancy, then said quantity is that which is mixed with buffer and lyophilized.

When it may become desirable to measure the amount of any endotoxin content in an aqueous liquid the content of the vial is reconstituted with 11 ml of water. In typical practice, 1 ml of the diluted lysate is added to each of several test tubes. At zero time, 0.1 ml of a series of known endotoxin standards and likewise of the unknown samples are added, respectively, to each tube. After incubating for 60 minutes at 37° C, the content of each tube is mixed by swirling and transferred to a microcuvette wherein absorbancy at 360 nm is determined. A similar reading is made in the case of a reagent control and this reading is subtracted from the other readings. The endotoxin absorbancy readings obtained in the case of the series of known endotoxin standards are plotted to provide a curve which may be used as applicable to the particular lysate in question. The endotoxin content of the unknown samples is then obtained directly from the standard curve so produced.

While one of the features and principal advantages of this invention is that of providing improved means whereby the presence of an endotoxin in an aqueous liquid may be quantitatively determined, this invention also may be availed of to provide a qualitative indication as to the presence of an endotoxin merely by mixing a quantity of lysate which has been established as being within the aforesaid critical concentration range with a quantity of an aqueous liquid to be tested for the possible presence therein of an endotoxin. After incubation favorable to turbidity development the mixture lends itself to ordinary visual inspection as regards the occurrence of turbidity. Preferably, any such observed turbidity is compared with a predetermined turbidity level such as that resulting from similarly producing a mixture that is similar except for the use of a standard solution having a predetermined endotoxin content such as 1.0 ng of standard endotoxin per ml, any turbidity above the predetermined level being regarded as indicative of an excessively pyrogenic liquid. When carrying out the invention in this way it usually is convenient to work with lesser liquid quantities than those above exemplified. For example, the volume of buffered lysate that is produced and lyophilized and that provides when reconstituted with water a solution within the aforesaid critical concentration range may be only one-tenth the volume utilized in accordance with the preceding example, the lyophilized lysate thereafter being reconstituted with only 1 ml of water in a single test vial. To this vial a standard quantity to the solution to be tested is added, e.g. 0.1 ml. After incubation for a specified time and temperature such as 1 hour at 37° C, a control tube and the test vial are visibly compared for turbidity. As aforesaid, the turbidity may be further compared with the turbidity obtained in a similar manner in the case of a solution having a predetermined endotoxin level. The practice of this invention in this manner provides a qualitative test. The qualitative testing may be used, for example, as a screening procedure for the detection of liquids which exhibit a positive response to the presence of endotoxin. Any such liquid could and probably would thereafter be rechecked by the quantitative procedures hereinabove described using appropriate instrumentation such as a spectrophotometer for precise measurement of absorbancy.

We claim:

1. In a method for determining the endotoxin content of an aqueous liquid wherein the protein content of an aqueous lysate of washed amebocyte cells from the blood of the horseshoe crab is coagulated responsive to endotoxin contained in a sample of the liquid, the improvement which comprises admixing a sample of the liquid with lysate which is the product of water lysing washed amebocyte cells, said lysate being buffered at a pH between about 6.5 and about 6.8 and being at a concentration such that 1 ml thereof is reactive with 0.1 ml of an endotoxin solution containing 1 ng per ml of endotoxin to develop upon incubation for 60 minutes at 37° C turbidity that imparts an absorbancy between about 0.07 and about 0.2 at 360 nm, incubating said admixture under temperature and time conditions conducive to an increase in absorbancy resulting from reaction of said lysate with any endotoxin contained in the sample, and determining the absorbancy of the incubated admixture.

2. The method according to claim 1 wherein the adsorbancy is determined by quantitative measurement.

3. The method according to claim 1 wherein the adsorbancy is determined by visual inspection.

4. The method according to claim 1 wherein 0.1 of the aqueous liquid is admixed with 1 ml of said lysate.

5. The method according to claim 1 wherein the adsorbancy determined as recited in claim 1 is compared with adsorbancy determined in like manner by reaction of the same lysate with one or more solutions of known endotoxin concentration.

6. The method according to claim 5 wherein the adsorbancy is determined by quantitatively measuring the adsorbancy of light of a given wavelength.

7. The method according to claim 1 wherein the concentration of said lysate as initially produced by lysing is substantially greater than the required concentration defined in claim 1, a quantity of the more concentrated lysate is admixed with a buffer adapted to provide a pH between about 6.5 and about 6.8 when said more concentrated lysate is diluted to provide the aforesaid required concentration, said buffered lysate is reduced to dryness by lyophilization, and the lyophilized buffered lysate is reconstituted with water to provide said required concentration prior to admixture of the lysate with a sample of the liquid to be tested.

8. The method according to claim 7 wherein a quantity of the more concentrated lysate is diluted, the diluted lysate is buffered at a pH between 6.5 and 6.8, and the buffered diluted solution is reacted with an endotoxin solution of known endotoxin content to provide a known lysate concentration metting the requirements recited in claim 1 and a like quantity of the more concentrated lysate is reduced to dryness in admixture with said buffer, and the lyophilized buffered lysate is reconstituted with water to provide a concentration in conformity with that recited in claim 1.

9. The method according to claim 1 wherein the admixture of the sample and the buffered lysate is incubated for 60 minutes at 37° C and the absorbancy at 360 nm is measured at the conclusion of the incubation period.

10. The method according to claim 1 wherein the washed amebocyte cells are lysed with a volume of pure water approximately twice the volume of the amebocyte cells from which the washing liquid has been drained.

11. The method according to claim 1 wherein said buffer comprises pipes buffer in effective amount for substantially stabilizing the buffered lysate when lyophilized and stored for three days at 40° C.

12. The method according to claim 1 wherein said buffer consists substantially entirely of pipes buffer.

13. A method according to claim 1 wherein said buffer comprises pipes buffer and phosphate buffer in substantially equal proportions.

14. An aqueous reagent composition for determining the presence of an endotoxin in an aqueous liquid, said aqueous reagent composition being an aqueous lysate of washed amebocyte cells from the blood of the horseshoe crab, said lysate being buffered at a pH between about 6.5 and 6.8 and being at a concentration such that 1 ml thereof is reactive with 0.1 ml of an endotoxin solution containing 1 ng per ml of endotoxin to develop upon incubation for 60 minutes at 37° C turbidity that imparts an absorbancy between about 0.07 and about 0.2 at 360 nm.

15. An aqueous reagent composition according to claim 14 wherein said buffer is selected from the group consisting of phosphate buffer and pipes buffer.

16. An aqueous reagent composition according to claim 15 wherein the buffer is about 0.0125 M.

17. An aqueous reagent composition according to claim 15 wherein said buffer comprises a mixture of phosphate buffer at about 0.0125 M and pipes buffer at about 0.0125 M.

18. An aqueous reagent composition according to claim 14 wherein said buffer comprises pipes buffer.

19. A method for preparing the aqueous reagent composition of claim 14 comprising adding an amount of water appropriate for providing the claimed required concentration of lysate to a dry reagent composition containing a lyophilized aqueous lysate of washed amebocyte cells from the blood of the horseshoe crab and a buffer, said buffer being sufficient to provide a pH between about 6.5 and about 6.8 when the lyophilized lysate is reconstituted with water to said concentration of lysate.

* * * * *

UNITED STATES PATENT AND TRADEMARK OFFICE
CERTIFICATE OF CORRECTION

PATENT NO. : 4,038,029
DATED : July 26, 1977
INVENTOR(S) : Joseph D. Teller and Kristine M. Kelly It is certified that error appears in the above-identified patent and that said Letters Patent are hereby corrected as shown below:

Col. 5, lines 38-39, delete "0.0125M pipes buffer and a mixture of 0.0125M phosphate buffer,"

Col. 6, line 19, delete "be" (first appearance), and substitute --then--

In Claims 2, 3, 5 and 6 delete the word "adsorbancy" in all instances and substitute therefor --absorbancy--

Signed and Sealed this

Tenth Day of January 1978

[SEAL]

Attest:

RUTH C. MASON
Attesting Officer

LUTRELLE F. PARKER
Acting Commissioner of Patents and Trademarks